United States Patent
Kuboki et al.

(10) Patent No.: US 11,958,940 B2
(45) Date of Patent: Apr. 16, 2024

(54) MALEIMIDE RESIN, CURABLE RESIN COMPOSITION, AND CURED PRODUCT THEREOF

(71) Applicant: NIPPONKAYAKU KABUSHIKI KAISHA, Tokyo (JP)

(72) Inventors: Kenichi Kuboki, Tokyo (JP);
Masataka Nakanishi, Tokyo (JP);
Kazuki Matsuura, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 685 days.

(21) Appl. No.: 17/254,850

(22) PCT Filed: Sep. 6, 2019

(86) PCT No.: PCT/JP2019/035152
§ 371 (c)(1),
(2) Date: Dec. 21, 2020

(87) PCT Pub. No.: WO2020/054601
PCT Pub. Date: Mar. 19, 2020

(65) Prior Publication Data
US 2021/0261736 A1 Aug. 26, 2021

(30) Foreign Application Priority Data
Sep. 12, 2018 (JP) ................................ 2018-170159

(51) Int. Cl.
*C08G 73/12* (2006.01)
*C07D 207/452* (2006.01)

(52) U.S. Cl.
CPC ....... *C08G 73/128* (2013.01); *C07D 207/452* (2013.01)

(58) Field of Classification Search
CPC ......................... C07D 207/452; C08G 73/128
See application file for complete search history.

(56) References Cited

U.S. PATENT DOCUMENTS

| 4,654,407 A | 3/1987 | Domeier |
| 4,743,647 A | 5/1988 | Domeier |

FOREIGN PATENT DOCUMENTS

| CN | 1062544 | 7/1992 | | |
| CN | 106084184 | 11/2016 | | |
| CN | 106103534 | 11/2016 | | |
| DE | 19532379 A1 | * | 3/1996 | ......... C07D 207/452 |
| EP | 390565 A | * | 10/1990 | ............ B32B 27/04 |

(Continued)

OTHER PUBLICATIONS

Machine-generated English-language translation of JP-2016023195-A.*

(Continued)

*Primary Examiner* — Vu A Nguyen
(74) *Attorney, Agent, or Firm* — JCIPRNET (57) ABSTRACT

Provided is a maleimide resin with superior solution stability. Also provided is a cured product with a superior dielectric characteristic that is obtained by curing a curable resin composition in which said maleimide resin is used. The maleimide resin expressed in formula (1), wherein the N,N'-(phenylene-di-(2,2,-propylidene)-di-p-phenylene) bis-maleimide content is 90 area % or less. (In formula (1), n is the number of repetitions, and 1<n<5.)

14 Claims, 5 Drawing Sheets

(56) References Cited

FOREIGN PATENT DOCUMENTS

| | | | |
|---|---|---|---|
| JP | S5430440 | 10/1979 | |
| JP | S63500866 | 3/1988 | |
| JP | H03100016 | 4/1991 | |
| JP | H03223331 | 10/1991 | |
| JP | H04222862 | 8/1992 | |
| JP | H0475222 | 11/1992 | |
| JP | H0637465 | 5/1994 | |
| JP | 2001316429 | 11/2001 | |
| JP | 5030297 | 9/2012 | |
| JP | 2016023195 A * | 2/2016 | |
| WO | WO-8700835 A1 * | 2/1987 | ......... C07D 207/444 |
| WO | WO-2017170551 A1 * | 10/2017 | .............. C08F 22/40 |

OTHER PUBLICATIONS

Machine-generated English-language translation of WO-2017170551-A1.*
"Office Action of China Counterpart Application", dated Feb. 21, 2023, with English translation thereof, p. 1-p. 15.
International Preliminary Report on Patentability (Form PCT/IB/373) of PCT/JP2019/035152, dated Mar. 9, 2021, with English translation thereof, pp. 1-11.
"International Search Report (Form PCT/ISA/210) of PCT/JP2019/035152", dated Nov. 26, 2019, with English translation thereof, pp. 1-4.
"Office Action of Taiwan Counterpart Application", dated Apr. 24, 2023, with English translation thereof, p. 1-p. 9.
Office Action of China Counterpart Application, with English translation thereof, dated Nov. 1, 2022, pp. 1-9.

* cited by examiner

MALEIMIDE RESIN, CURABLE RESIN COMPOSITION, AND CURED PRODUCT THEREOF

CROSS-REFERENCE TO RELATED APPLICATION

This application is a 371 application of the International PCT application serial no. PCT/JP2019/035152, filed on Sep. 6, 2019, which claims the priority benefit of Japan Patent Application No. 2018-170159, filed on Sep. 12, 2018. The entirety of each of the above-mentioned patent applications is hereby incorporated by reference herein and made a part of this specification.

TECHNICAL FIELD

The present invention relates to a maleimide resin having excellent solution stability, a curable resin composition using the same and a cured product thereof, and is suitably used for an electrical and electronic component such as a semiconductor encapsulant, a printed wiring board, and a build-up laminated plate and a lightweight and high strength material such as a carbon fiber-reinforced plastic and a glass fiber-reinforced plastic.

BACKGROUND ART

In recent years, laminated plates on which electrical and electronic components are mounted have come to have broader and more sophisticated required characteristics due to expansion of their field of use. For example, in the related art, semiconductor chips have been mainly mounted on metal lead frames, but semiconductor chips having high processing power such as CPUs have been mounted on laminated plates made of polymer materials in many cases. When the speed of elements such as CPUs increases and the clock frequency increases, there are problems of signal propagation delay and transmission loss, and a low dielectric constant and a low dielectric loss tangent are required for a wiring board. At the same time, as the speed of elements increases, since the amount of heat generated from chips increases, it is necessary to increase the heat resistance. In addition, in recent years, since mobile electronic devices such as mobile phones have become widespread, and precision electronic devices have come to be used in outdoor environments and used in the immediate vicinity of the human body or held by humans, they need to have resistance with respect to external environments (in particular, a moist and hot environment). In addition, in the field of automobiles, digitalization is progressing rapidly, precision electronic devices may be disposed near the engine, and higher level of heat resistance and moisture resistance are required. In addition, safety such as flame retardance is becoming more important because of use in automobile applications and mobile devices. However, there is an increasing need to impart flame retardance without using halogens because use of halogen flame retardants is being avoided due to recent increased environmental awareness.

In the related art, for example, a wiring board using a BT resin which is a resin in which a bisphenol A type cyanate ester compound and a bismaleimide compound are used in combination as in Patent Literature 1 has an excellent heat resistance, chemical resistance, and electrical characteristics, and is widely used as a high-performance wiring board, but improvement is necessary under a circumstance in which higher performance is required as described above.

In addition, in recent years, the weights of airplanes, automobiles, trains, ships, and the like have been reduced in consideration of energy saving. Studies in which a lightweight and high-strength carbon fiber composite material is used for objects for which a metal material was used in the related art have been particularly conducted in the field of vehicles. For example, in the Boeing 787, the weight is reduced by increasing the proportion of a composite material and the fuel efficiency is significantly improved. In the field of aviation, in order to further reduce the weight, there is a trend to introduce a carbon fiber composite material into members around the engine, and a high level of heat resistance is naturally required. In the field of automobiles, although this only applies for some parts, a propeller shaft made of a composite material may be mounted and there is a movement of making a vehicle body with a composite material for luxury vehicles. In the field of carbon fiber composite materials, in the related art, composite materials using bisphenol A type diglycidyl ether for an epoxy resin, tetraglycidyl diaminodiphenylmethane or the like and diaminodiphenylmethane, diaminodiphenyl sulfone, or the like as a curing agent are used. However, in order to further reduce the weight and achieve high heat resistance, it is necessary to expand a range of composite material applications, and a maleimide resin is being studied as one material for that purpose.

In these situations, commercially available maleimide compounds are often bismaleimide compounds, and since they are crystals having a high melting point, it is necessary to use them in the form of a solution. However, they have disadvantages that they are unlikely to dissolve in a general purpose organic solvent and are only soluble in a solvent having a high boiling point and high hygroscopicity such as N,N-dimethylacetamide and N-methyl-2-pyrrolidone. In addition, a cured product of a bismaleimide compound has favorable heat resistance but it has disadvantages that it is brittle and has high hygroscopicity.

On the other hand, as in Patent Literature 2 and 3, maleimide resins having a molecular weight distribution, a relatively low softening point, and better solubility in solvents than bismaleimide compounds in the related art have been developed but they are not yet sufficient.

REFERENCE LIST

Patent Literature

Patent Literature 1: Japanese Examined Patent Publication No. S54-30440
Patent Literature 2: Japanese Patent Laid-Open No. H3-100016
Patent Literature 3: Japanese Patent No. 5030297
Patent Literature 4: Japanese Examined Patent Publication No. H4-75222
Patent Literature 5: Japanese Examined Patent Publication No. H6-37465

SUMMARY

Technical Problem

An objective of the present invention is to produce a maleimide resin having excellent solution stability at low cost, improve workability in preparing a curable resin composition, and expand the range of the composition. In addition, an objective of a cured product of the maleimide resin of the present invention is to realize a lower dielectric constant and lower dielectric loss tangent than when other maleimide resins are used.

Solution to Problem

The inventors conducted extensive studies in order to address the above problems and as a result, completed the present invention.

Specifically, the present invention relates to the following [1] to [8].

[1] A maleimide resin represented by the following Formula (1) and in which the content of N,N'-(phenylene-di-(2,2-propylidene)-di-p-phenylene)bismaleimide is 90 area % or less:

(1)

(in Formula (1), n represents the number of repetitions, and 1<n<5).

[2] The maleimide resin according to [1],
wherein the content of the component having n=1 in Formula (1) is 98 area % or less.

[3] A maleimide resin represented by the following Formula (2) and in which the content of N,N'-(1,3-phenylene-di-(2,2-propylidene)-di-p-phenylene) bismaleimide is 90 area % or less:

(2)

(in Formula (2), n represents the number of repetitions, and 1<n<5).

[4] The maleimide resin according to [3],
wherein the content of the component having n=1 in Formula (2) is 98 area % or less.

[5] A maleimide resin obtained by reacting an aromatic amine resin represented by the following Formula (3) with maleic acid or maleic anhydride, and which is a maleimide resin containing 90 area % or less of N,N'-(phenylene-di-(2,2-propylidene)-di-p-phenylene)bismaleimide and represented by the following Formula (1):

(3)

(in Formula (3), n represents the number of repetitions, and 1<n<5)

(1)

(in Formula (1), n represents the number of repetitions, and 1<n<5.)

[6] A curable resin composition containing the maleimide resin according to any one of [1] to [5].

[7] The curable resin composition according to [6], further including
a curing agent.

[8] A cured product obtained by curing the curable resin composition according to [6] or [7].

Advantageous Effects of Invention

The maleimide resin of the present invention can be produced at low cost and has excellent solution stability and significantly improves workability, and a dielectric constant and a dielectric loss tangent can be kept low in a cured product of the curable resin composition using the same.

DESCRIPTION OF THE EMBODIMENTS

Hereinafter, the present invention will be described in detail. First, a method of producing a maleimide resin of the present invention will be described.

[Method of Producing Aromatic Amine Resin]

For a maleimide resin of the present invention, an aromatic amine resin represented by the following Formula (3) can be used as a precursor.

(3)

(in Formula (3), n represents the number of repetitions, and 1<n<5).

An aromatic amine resin represented by Formula (3) is more preferably represented by the following Formula (4). This is because in this case the crystallinity is lower than when the substitution position of the propyl group with respect to a benzene ring to which an amino group is not bonded is the para position in Formula (3).

(4)

(in Formula (4), n represents the number of repetitions, and 1<n<5)

A method of producing an aromatic amine resin represented by Formula (3) or Formula (4) is not particularly limited. For example, in Patent Literature 4, aniline and m-diisopropenylbenzene or m-di(α-hydroxyisopropyl)benzene are reacted in the presence of an acid catalyst at 180 to 250° C., and the component having n=1 in Formula (4) is obtained as a main component, and three isomers including 1,3-bis(p-aminocumyl)benzene, 1-(o-aminocumyl)-3-(p-aminocumyl)benzene, and 1,3-bis(o-aminocumyl)benzene are contained therein. In addition, although n=2 to 5 components are also generated as subcomponents, in Patent Literature 4, these are removed by crystallization to obtain 1,3-bis(p-aminocumyl)benzene having a purity of 98%. In addition, in Patent Literature 5, 1,3-bis(p-aminocumyl)benzene is formed into a maleimide and N,N'-(1,3-phenylene-di-(2,2-propylidene)-di-p-phenylene)bismaleimide is synthesized to obtain a crystal product. However, heating is necessary to dissolve this product in a solvent, and if this product is left at room temperature after heating, crystals may precipitate in a few hours. Therefore, crystals may precipitate if the resin composition is prepared, and when the concentration of N,N'-(1,3-phenylene-di-(2,2-propylidene)-di-p-phenylene)bismaleimide is higher, the probability of crystallization is higher. In order to produce a printed wiring board and a composite material, glass cloth or carbon fibers are impregnated with a varnish to adhere the resin, but if crystals precipitate, an impregnation operation is not possible. On the other hand, if the temperature is raised to maintain the dissolved state, the reaction of the composition will be accelerated and the pot life of the varnish will be shortened.

In the present invention, focusing on isomers and polymer components in the aromatic amine resin that were removed as insoluble components in Patent Literature 4, a maleimide resin having excellent solution stability has been developed by forming a maleimide without removing these.

Since the present invention does not require a purifying process such as crystallization, production can be performed in a short time and at low cost, and industrial applicability can be improved.

Examples of acid catalysts used when the aromatic amine resin represented by Formula (3) is synthesized include acid catalysts such as hydrochloric acid, phosphoric acid, sulfuric acid, formic acid, zinc chloride, ferric chloride, aluminum chloride, p-toluenesulfonic acid, methanesulfonic acid, activated clay, and an ion exchange resin. These may be used alone or two or more thereof may be used in combination. The amount of the catalyst used is generally 0.1 to 50 weight % and preferably 1 to 30 weight % with respect to the aniline used. When the amount is too large, the viscosity of the reaction solution is too large, and stirring becomes difficult, and when the amount is too small, the progress of the reaction becomes slow.

The reaction may be performed using an organic solvent such as toluene and xylene as necessary or may be performed without a solvent. For example, after an acid catalyst is added to a solution in which aniline and a solvent are mixed, if the catalyst contains water, it is preferable to remove water from the system using an azeotrope. Thereafter, diisopropenylbenzene or di(α-hydroxyisopropyl)benzene is added, the temperature is then raised while removing the solvent from the system, and the reaction is performed at 140 to 220° C., preferably 160 to 200° C. for 5 to 50 hours, and preferably for 5 to 30 hours. When di(α-hydroxyisopropyl)benzene is used, since water is produced as a by-product, it is removed from the system while forming an azeotrope with the solvent when the temperature rises. After the reaction is completed, the acid catalyst is neutralized with an alkaline aqueous solution, a water-insoluble organic solvent is then added to an oil layer, washing with water is repeated until wastewater becomes neutral, and the solvent and excess aniline derivatives are then removed by heating under a reduced pressure. When activated clay or an ion exchange resin is used, after the reaction is completed, the reaction solution is filtered and the catalyst is removed.

In addition, since diphenylamine is produced as a by-product depending on the reaction temperature and the type of the catalyst, under a high temperature and a high vacuum, or using a method such as steam distillation, diphenylamine derivatives are removed so that the content is 1 weight % or less, preferably 0.5 weight % or less, and more preferably 0.2 weight % or less.

The maleimide resin of the present invention can be obtained by adding or dehydrating or condensing the aromatic amine resin represented by Formula (3) obtained in the above process with respect to maleic acid or maleic anhydride (hereinafter referred to as a "maleic anhydride") in the presence of a solvent and a catalyst.

[Method of Producing Maleimide Resin]

Regarding a solvent used in the reaction, a water-insoluble solvent is used because it is necessary to remove water produced during the reaction from the system. Examples thereof include aromatic solvents such as toluene and xylene, aliphatic solvents such as cyclohexane and n-hexane, ethers such as diethyl ether and diisopropyl ether, ester solvents such as ethyl acetate and butyl acetate, ketone solvents such as methyl isobutyl ketone and cyclopentanone, and the present invention is not limited thereto and two or more thereof may be used in combination.

In addition, in addition to the water-insoluble solvent, an aprotic polar solvent can be used in combination. Examples thereof include dimethyl sulfone, dimethyl sulfoxide, dimethylformamide, dimethylacetamide, 1,3-dimethyl-2-imidazolidinone, and N-methyl-2-pyrrolidone, and two or more thereof may be used in combination. When an aprotic polar solvent is used, it is preferable to use a solvent having a boiling point higher than that of the water-insoluble solvent used in combination therewith.

In addition, the catalyst used in the reaction is an acid catalyst and is not particularly limited, and examples thereof include p-toluenesulfonic acid, hydroxy-p-toluenesulfonic acid methanesulfonic acid, sulfuric acid, and phosphoric acid. The amount of the acid catalyst used is generally 0.1 to 10 weight % and preferably 1 to 5 weight % with respect to the aromatic amine resin.

For example, the aromatic amine resin represented by Formula (3) is dissolved in toluene and N-methyl-2-pyrrolidone, and maleic anhydride is added thereto to produce an amic acid, p-toluenesulfonic acid is then added thereto, and the reaction is performed while removing water produced under reflux conditions from the system.

In addition, maleic anhydride is dissolved in toluene, an N-methyl-2-pyrrolidone solution containing the aromatic amine resin represented by Formula (3) is added under stirring to produce an amic acid, p-toluenesulfonic acid is then added, and the reaction is performed while removing water produced under reflux conditions from the system.

In addition, maleic anhydride is dissolved in toluene, and p-toluenesulfonic acid is added, and while an N-methyl-2-pyrrolidone solution containing the aromatic amine resin represented by Formula (3) in a stirred and refluxed state is added dropwise thereto, water that forms an azeotropic composition is removed from the system during this, and toluene reacts while returning into the system (the above is a first stage reaction).

In any of the methods, maleic anhydride is used in an amount of generally 1 to 3 equivalents and preferably 1.2 to 2.0 equivalents with respect to the amino group of the aromatic amine resin represented by Formula (3).

In order to reduce the amount of unclosed ring amic acid, water is added to the reaction solution after the maleimization reaction listed above, separation into a resin solution layer and an aqueous layer is performed, excess maleic acid, maleic anhydride, an aprotic polar solvent, a catalyst, and the like are dissolved in the aqueous layer, and thus these are removed by liquid separation, and additionally, the same operation is repeated, and the excess maleic acid, maleic anhydride, aprotic polar solvent, and catalyst are removed thoroughly. When a catalyst is added again to a maleimide resin solution in an organic layer from which the excess maleic acid, maleic anhydride, aprotic polar solvent, and catalyst have been removed, a dehydration ring closure reaction of the residual amic acid is performed again under heating and reflux conditions, and thus a maleimide resin solution having a low acid value is obtained (the above is a second stage reaction).

The re-dehydration ring closure reaction time is generally 1 to 5 hours, and preferably 1 to 3 hours, and the above aprotic polar solvent may be added as necessary. After the reaction is completed, cooling is performed and washing with water is repeated until washing water becomes neutral. Then, water is removed using azeotropic dehydration by heating under a reduced pressure, and the solvent is then distilled off, or another solvent may be added to prepare a resin solution having a desired concentration, the solvent may be completely distilled off and a solid resin may be extracted.

The maleimide resin of the present invention obtained by the above production method has a structure represented by the following Formula (1).

(1)

(in Formula (1), n represents the number of repetitions, and $1<n<5$)

In Formula (1), the value of n can be calculated from the value of the number average molecular weight obtained by analysis of the maleimide resin by gel permeation chromatography (GPC, detector: RI), but it can be considered to be approximately almost the same as the value of n calculated from GPC measurement results of the aromatic amine resin represented by Formula (3) which is a raw material.

In the present invention, the content of N,N'-(phenylene-di-(2,2-propylidene)-di-p-phenylene)bismaleimide is determined by the following method.

First, the content (x) of the component having n=1 in Formula (1) is determined according to gel permeation chromatography (GPC, detector: RI) analysis. Subsequently, the content (y) of N,N'-(phenylene-di-(2,2-propylidene)-di-p-phenylene)bismaleimide in the component having n=1 is determined according to high performance liquid chromatography (HPLC) analysis.

N,N'-(phenylene-di-(2,2-propylidene)-di-p-phenylene) bismaleimide in maleimide represented by Formula (1) is calculated by a calculation formula $(x)\times(y)$.

The content of N,N'-(phenylene-di-(2,2-propylidene)-di-p-phenylene) bismaleimide in the maleimide resin of the present invention is in a range of generally 90 area % or less, preferably 10 to 80 area %, more preferably 20 to 80 area %, and still more preferably 30 to 70 area %. When the content of N,N'-(phenylene-di-(2,2-propylidene)-di-p-phenylene) bismaleimide is 90 area % or less, since the crystallinity is lowered, the solubility in solvents is improved. On the other hand, the lower limit value of N,N'-(phenylene-di-(2,2-propylidene)-di-p-phenylene)bismaleimide may be 0 area %, but if it is 10 area % or more, decrease in reactivity can be minimized.

The content of the component having n=1 in the maleimide resin of the present invention determined according to GPC analysis (RI) is in a range of preferably 98 area % or less, more preferably 20 to 98 area %, still more preferably 30 to 90 area %, and particularly preferably 40 to 80 area %. When the content of the component having n=1 is 98 area % or less, the heat resistance becomes favorable. On the other hand, the lower limit value of the component having n=1 may be 0 area %, and if the value is 20 area % or more, the viscosity of the resin solution is lowered and impregnation properties become favorable.

The softening point of the maleimide resin of the present invention is preferably 50° C. to 150° C., more preferably 80° C. to 120° C., still more preferably 90° C. to 110° C., and particularly preferably 95° C. to 100° C. In addition, the melt viscosity at 150° C. is 0.05 to 100 Pa·s and preferably 0.1 to 40 Pa·s.

The maleimide resin of the present invention more preferably has a structure represented by Formula (2). This is because in this case the crystallinity is lower than when the substitution position of the propyl group with respect to a benzene ring to which a maleimide group is not bonded is the para position in Formula (1).

(2)

(in Formula (2), n represents the number of repetitions, and 1<n<5)

Next, a curable resin composition of the present invention will be described.

The curable resin composition of the present invention can contain a compound that can crosslink with a maleimide resin of the present invention. The compound is not particularly limited as long as it is a compound having a functional group (or a structure) that can crosslink with a maleimide resin such as an amino group, a cyanate group, a phenolic hydroxyl group, an alcoholic hydroxyl group, an allyl group, a methallyl group, an acryloyl group, a methacrylic group, a vinyl group, and a conjugated diene group.

Since an amine compound and a maleimide compound undergo a crosslinking reaction, the aromatic amine resin represented by Formula (3) may be used. Since the maleimide resin can be self-polymerized, it can be used alone. In addition, an amine compound other than the aromatic amine resin represented by Formula (3) or a maleimide compound other than the maleimide resin of the present invention represented by Formula (1) may be used in combination.

The content of the maleimide resin in the curable resin composition of the present invention is preferably 10 weight % or more, more preferably 15 weight % or more, and still more preferably 20 weight %. Within the above range, regarding physical properties of the cured product, the mechanical strength tends to increase, the peel strength tends to increase, and additionally, the heat resistance tends to increase.

Conventionally known amine compounds can be used as an amine compound that can be incorporated into the curable resin composition of the present invention. Specific examples of amine compounds include diethylenetriamine, triethylenetetramine, tetraethylenepentamine, m-xylenediamine, trimethylhexamethylenediamine, 2-methylpentamethylenediamine, diethylaminopropylamine, isophoronediamine, 1,3-bisaminomethylcyclohexane, bis(4-aminocyclohexyl)methane, bis(4-amino-3-methylcyclohexyl)methane, norbornene diamine, 1,2-diaminocyclohexane, diaminodiphenylmethane, metaphenylenediamine, diaminodiphenyl sulfone, dicyandiamide, polyoxypropylene diamine, polyoxypropylene triamine, N-aminoethylpiperazine, and an aniline/formalin resin, but the present invention is not limited thereto. These may be used alone or two or more thereof may be used in combination.

In addition, the aromatic amine resin described in the scope of claims of Patent Literature 3 is particularly preferable because it has an excellent low hygroscopicity, flame retardance, and dielectric characteristics.

Conventionally known maleimide compounds can be used as a maleimide compound that can be incorporated into the curable resin composition of the present invention. Specific examples of maleimide compounds include 4,4'-diphenylmethane bismaleimide, polyphenylmethane maleimide, m-phenylene bismaleimide, 2,2'-bis[4-(4-maleimide phenoxy)phenyl]propane, 3,3'-dimethyl-5,5'-diethyl-4,4'-diphenylmethane bismaleimide, 4-methyl-1,3-phenylene bismaleimide, 4,4'-diphenyl ether bismaleimide, 4,4'-diphenyl sulfone bismaleimide, 1,3-bis(3-maleimide phenoxy)benzene, 1,3-bis(4-maleimide phenoxy)benzene, but the present invention is not limited thereto. These may be used alone or two or more thereof may be used in combination. The amount of the maleimide compound incorporated is in a range of preferably 5 times or less, and more preferably 2 times or less the amount of the maleimide resin of the present invention in terms of weight ratio.

In addition, the maleimide resin in claims of Patent Literature 3 is particularly preferable because it has an excellent low hygroscopicity, flame retardance, and dielectric characteristics.

Conventionally known cyanate ester compounds can be used as a cyanate ester compound that can be incorporated into the curable resin composition of the present invention. Specific examples of cyanate ester compounds include cyanate ester compounds that can be obtained by reacting polycondensates of phenols and various aldehydes, polymers of phenols and various diene compounds, polycondensates of phenols and ketones and polycondensates of bisphenols and various aldehydes with halogenated cyanates, but the present invention is not limited thereto. These may be used alone or two or more thereof may be used in combination.

Examples of phenols include phenol, alkyl-substituted phenol, aromatic-substituted phenol, naphthol, alkyl-substituted naphthol, dihydroxybenzene, alkyl-substituted dihydroxybenzene, and dihydroxynaphthalene.

Examples of various aldehydes include formaldehyde, acetaldehyde, alkylaldehydes, benzaldehyde, alkyl-substituted benzaldehyde, hydroxybenzaldehyde, naphthaldehyde, glutaraldehyde, phthalaldehyde, crotonaldehyde, and cinnamaldehyde.

Examples of various diene compounds include dicyclopentadiene, terpenes, vinyl cyclohexene, norbornadiene, vinyl norbornene, tetrahydroindene, divinylbenzene, divinylbiphenyl, diisopropenylbiphenyl, butadiene, and isoprene.

Examples of ketones include acetone, methyl ethyl ketone, methyl isobutyl ketone, acetophenone, and benzophenone.

In addition, a cyanate ester compound whose synthesis method is described in Japanese Patent Laid-Open No. 2005-264154 is particularly preferable as a cyanate ester compound because it has an excellent low hygroscopicity, flame retardance, and dielectric characteristics.

An epoxy resin can further be incorporated into the curable resin composition of the present invention. Regarding the epoxy resin that can be incorporated, any of conventionally known epoxy resins can be used. Specific examples of epoxy resins include glycidyl ether epoxy resins obtained by glycidylizing polycondensates of phenols and various aldehydes, polymers of phenols and various diene compounds, polycondensates of phenols and ketones, polycondensates of bisphenols and various aldehydes and alcohols, alicyclic epoxy resins typified as 4-vinyl-1-cyclohexene diepoxide and 3,4-epoxycyclohexylmethyl-3,4'-epoxycyclohexanecarboxylate, glycidylamine epoxy resins typified as tetraglycidyl diaminodiphenylmethane (TGDDM) and triglycidyl-p-aminophenol, and glycidyl ester epoxy resins, but the present invention is not limited thereto. These may be used alone or two or more thereof may be used in combination.

In addition, an epoxy resin obtained by a dehydrochlorination reaction with epichlorohydrin using a phenolic aralkyl resin obtained from a condensation reaction of phenols and bishalogenomethyl aralkyl derivatives or aralkyl alcohol derivatives as raw materials is particularly preferable as an epoxy resin because it has an excellent low hygroscopicity, flame retardance, and dielectric characteristics.

When the epoxy resin is incorporated, the formulation amount is not particularly limited, and it is in a range of preferably 0.1 to 10 times, and more preferably 0.2 to 4 times the amount of the maleimide resin in terms of weight ratio. When the formulation amount of the epoxy resin is 0.1 times or less the amount of the maleimide resin, there is a risk of the cured product becoming brittle, and when it is 10 times or more, there is a risk of dielectric characteristics deteriorating.

In the curable resin composition of the present invention, a compound including a phenolic resin can be further incorporated.

Any of conventionally known phenolic resins can be used as a phenolic resin that can be incorporated. Specific examples of phenolic resins include polycondensates of bisphenols (bisphenol A, bisphenol F, bisphenol S, bisphenol, bisphenol AD, etc.), phenols (phenol, alkyl-substituted phenol, aromatic-substituted phenol, naphthol, alkyl-substituted naphthol, dihydroxybenzene, alkyl-substituted dihydroxybenzene, dihydroxynaphthalene, etc.) and various aldehydes (formaldehyde, acetaldehyde, alkylaldehydes, benzaldehyde, alkyl-substituted benzaldehyde, hydroxybenzaldehyde, naphthaldehyde, glutaraldehyde, phthalaldehyde, crotonaldehyde, cinnamaldehyde, etc.), polymers of phenols and various diene compounds (dicyclopentadiene, terpenes, vinylcyclohexene, norbornadiene, vinyl norbornene, tetrahydroindene, divinylbenzene, divinylbiphenyl, diisopropenylbiphenyl, butadiene, isoprene, etc.), polycondensates of phenols and ketones (acetone, methyl ethyl ketone, methyl isobutyl ketone, acetophenone, benzophenone, etc.), polycondensates of phenols and aromatic dimethanols (benzene dimethanol, α,α,α',α'-benzene dimethanol, biphenyl dimethanol, α,α,α',α'-biphenyl dimethanol, etc.), polycondensates of phenols and aromatic dichloromethyls (α,α'-dichloroxylene, bischloromethylbiphenyl, etc.), polycondensates of bisphenols and various aldehydes, and modified products thereof, but the present invention is not limited thereto. These may be used alone or two or more thereof may be used in combination.

In addition, a phenolic aralkyl resin obtained from a condensation reaction between phenols and bishalogenomethyl aralkyl derivatives or aralkyl alcohol derivatives is particularly preferable as a phenolic resin because it has an excellent low hygroscopicity, flame retardance, and dielectric characteristics.

In addition, when the phenolic resin has an allyl group or a methallyl group, this is preferable because the reactivity with respect to the maleimide group is better than that with a hydroxy group, the curing rate increases and the number of crosslinking points increases, and thus the strength and the heat resistance are improved.

In addition, an allyl etheric component obtained by allylating the hydroxy group of a phenolic resin and a metallyl etheric component obtained by metallizing the hydroxy group can also be incorporated, and the water absorption is lowered because the hydroxy group is etherified.

In the curable resin composition of the present invention, a compound having an acid anhydride group can be further incorporated.

Any of conventionally known compounds can be used as a compound having an acid anhydride group that can be incorporated. Specific examples of a compound having an acid anhydride group include 1,2,3,4-butanetetracarboxylic dianhydride, 1,2,3,4-cyclobutanetetracarboxylic dianhydride, 1,2,3,4-cyclopentanetetracarboxylic dianhydride, 1,2,4,5-cyclohexanetetracarboxylic dianhydride, pyromellitic anhydride, 5-(2,5-dioxotetrahydrofuryl)-3-methyl-3-cyclohexene-1,2-dicarboxylic acid anhydride, and 4-(2,5-dioxotetrahydrofuran-3-yl)-1,2,3,4-tetrahydronaphthalene-1,2-dicarboxylic acid anhydride.

Compounds having an acid anhydride group can be used alone or two or more thereof can be used in combination. In addition, an acid anhydride group and an amine may be reacted and as a result, an amic acid is obtained, and when heating is additionally performed at 200° C. to 300° C., an imide structure is formed due to a dehydration reaction and a material having very excellent heat resistance is obtained.

A catalyst for curing (curing accelerator) can be incorporated into the curable resin composition of the present invention as necessary. Examples thereof include imidazoles such as 2-methylimidazole, 2-ethylimidazole, 2-phenylimidazole, 2-ethyl-4-methylimidazole, 2-undecylimidazole, and 1-cyanoethyl-2-ethyl-4-methylimidazole, amines such as triethylamine, triethylenediamine, 2-(dimethylaminomethyl)phenol, 1,8-diazabicyclo(5,4,0)undecene-7, tris(dimethylaminomethyl)phenol, and benzyldimethylamine, phosphines such as triphenylphosphine, tributylphosphine, and trioctylphosphine, organic metal salts such as tin octylate, zinc octylate, dibutyltin dimalate, zinc naphthenate, cobalt naphthenate, and tin oleate, metal chlorides such as zinc chloride, aluminum chloride, and tin chloride, organic peroxides such as di-tert-butyl peroxide and dicumyl peroxide, azo compounds such as azobisisobutyronitrile and azobisdimethylvaleronitrile, mineral acids such as hydrochloric acid, sulfuric acid, and phosphoric acid, Lewis acids such as boron trifluoride, and salts such as sodium carbonate and lithium chloride. The formulation amount of the catalyst for curing is in a range of preferably 10 parts by weight or less and more preferably 5 parts by weight or less with respect to a total of 100 parts by weight of the curable resin composition.

An organic solvent can be added to the curable resin composition of the present invention to obtain a varnish-like composition (hereinafter simply referred to as a varnish). Examples of solvents used include amide solvents such as γ-butyrolactones, N-methylpyrrolidone, N,N-dimethylformamide, N,N-dimethylacetamide, and N,N-dimethylimidazolidinone, sulfones such as tetramethylene sulfone, ether solvents such as diethylene glycol dimethyl ether, diethylene glycol diethyl ether, propylene glycol, propylene glycol monomethyl ether, propylene glycol monomethyl ether acetate, and propylene glycol monobutyl ether, ketone solvents such as methyl ethyl ketone, methyl isobutyl ketone, cyclopentanone, and cyclohexanone, and aromatic solvents such as toluene and xylene. The solvent is used in a range in which the concentration of the solid content of the obtained varnish excluding the solvent is generally 10 to 80 weight % and preferably 20 to 70 weight %.

Further, as necessary, known additives can be incorporated into the curable resin composition of the present invention. Specific examples of additives used include a curing agent for an epoxy resin, polybutadiene and modified products thereof, a modified product of an acrylonitrile copolymer, polyphenylene ether, polystyrene, polyethylene, polyimide, a fluorine resin, a maleimide compound, a cyanate ester compound, silicone gel, silicone oil, inorganic fillers such as silica, alumina, calcium carbonate, quartz powder, aluminum powder, graphite, talc, clay, iron oxide, titanium oxide, aluminum nitride, asbestos, mica, and glass powder, a surface treatment agent for a filler such as a silane coupling agent, a release agent, and a coloring agent such as carbon black, phthalocyanine blue, and phthalocyanine green. The formulation amount of these additives is in a range of preferably 1,000 parts by weight or less, and more preferably 700 parts by weight or less with respect to 100 parts by weight of the curable resin composition.

A method of preparing a curable resin composition of the present invention is not particularly limited, and components may be simply uniformly mixed or prepolymerized. For example, a maleimide resin and a cyanate ester compound may be prepolymerized by heating in the presence or in the absence of a catalyst and in the presence or in the absence of a solvent. Similarly, the maleimide resin of the present invention may be prepolymerized by adding an epoxy resin, an amine compound, a maleimide compound, a cyanate ester compound, a phenolic resin, an acid anhydride compound and other additives as necessary. For mixing or prepolymerizing components, in the absence of a solvent, for example, an extruder, a kneader, or a roller is used, and in the presence of a solvent, a reaction tank having a stirring device or the like is used.

A prepreg can be obtained by heating and melting the curable resin composition of the present invention, lowering the viscosity, and impregnating the composition into reinforcing fibers such as glass fibers, carbon fibers, polyester fibers, polyamide fibers, and alumina fibers.

In addition, a prepreg can be obtained by impregnating the varnish with reinforcing fibers and performing heating and drying.

The above prepreg is cut into a desired shape and laminated with a copper foil or the like as necessary, and a curable resin composition is then heated and cured while applying a pressure to the laminate by a press molding method, an autoclave molding method, a sheet winding molding method, or the like, and thus a laminated plate (printed wiring board) for electric and electronic components and a carbon fiber reinforcing material can be obtained.

EXAMPLES

Hereinafter, the present invention will be described in detail with reference to examples and comparative examples. Here, "parts" and "%" in the specification represent "parts by weight" and "weight %." The softening point and the melt viscosity are measured by the following methods.

Softening point: measured by a method according to JIS K-7234
Acid value: measured by a method according to JIS K-0070: 1992
GPC (Gel Permeation Chromatography) Analysis
Column: SHODEX GPC KF-601 (2 columns), KF-602, KF-602.5, KF-603
Flow rate: 0.5 ml/min
Column temperature: 40° C.
Solvent used: THF (tetrahydrofuran)
Detector: RI (differential refractometer detector)
HPLC (High Performance Liquid Chromatography) Analysis Column: Inertsil ODS-2
Flow rate: 1.0 ml/min
Column temperature: 40° C.
Solvent used: acetonitrile/water
Detector: photodiode array (200 nm)

Synthesis Example 1

279 parts of aniline, 100 parts of toluene, 146 parts of m-di(α-hydroxyisopropyl)benzene, and 50 parts of activated clay were put into a flask having a thermometer, a cooling pipe, a Dean-Stark azeotropic distillation trap, and a stirrer attached thereto, and the temperature inside the system was raised to 170° C. over 6 hours while distilling off water and toluene, and the reaction was performed at this temperature for 13 hours. Then, the mixture was cooled to room temperature, 230 parts of toluene was added, and activated clay was removed by filtration. Then, excess aniline and toluene were distilled off from the oil layer by heating under a reduced pressure using a rotary evaporator to obtain 241 parts of the aromatic amine resin (A1) represented by Formula (4). The amine equivalent of the aromatic amine resin (A1) was 179 g/eq, and the softening point was 46.5° C. Since the weight of the component having n=1 determined according to GPC analysis (RI) was 73%, and the weight of 1,3-bis(p-aminocumyl)benzene in the component having n=1 determined according to HPLC analysis was 49%, the weight of 1,3-bis(p-aminocumyl)benzene in the aromatic amine resin was 36%.

Synthesis Example 2

93 parts of aniline, 50 parts of toluene, and 52.1 parts of 35% hydrochloric acid were put into a flask having a thermometer, a cooling pipe, a Dean-Stark azeotropic distillation trap, and a stirrer attached thereto, and while raising the temperature, water and toluene were distilled off, the temperature inside the system was set to 165 to 170° C., 20 parts of 1,3-diisopropenylbenzene was added dropwise over 1.5 hours at this temperature, and the reaction was performed at the same temperature for 30 hours. Then, while cooling, 87 parts of a 30% sodium hydroxide aqueous solution was slowly added dropwise so that the inside of the system did not reflux exhaustively, 50 parts of toluene was added at 80° C. or lower, and the mixture was left at 70° C. to 80° C. The separated lower aqueous layer was removed, and washing of the reaction solution with water was repeated until the cleaning liquid became neutral. Next, excess aniline and toluene were distilled off from the oil layer by heating under a reduced pressure using a rotary evaporator and 100 parts of toluene was then added, heated and dissolved, 100 parts of cyclohexane was then added and crystallization, filtration and drying were performed, and 35 parts of 1,3-bis(p-aminocumyl)benzene (A2) having 100% of the component having n=1 according to GPC analysis (RI) and having a purity of 98% according to HPLC was obtained.

Example 1

147 parts of maleic anhydride, 300 parts of toluene, and 4 parts of methanesulfonic acid were put into a flask having a thermometer, a cooling pipe, a Dean-Stark azeotropic distillation trap, and a stirrer attached thereto, and brought into a heated and reflux state. Then, a resin solution prepared by dissolving 197 parts of the aromatic amine resin (A1) in 95 parts of N-methyl-2-pyrrolidone and 100 parts of toluene was added dropwise over 3 hours while maintaining a reflux state. During this period, condensed water and toluene which formed an azeotrope under reflux conditions were cooled and liquid-separated in the Dean-Stark azeotropic distillation trap, and then toluene on the organic layer was returned into the system, and water was discharged to the outside of the system. After dropwise addition of the resin solution was completed, the reaction was performed for 6 hours while maintaining a reflux state and performing a dehydration operation.

After the reaction was completed, washing with water was repeated 4 times, methanesulfonic acid and excess maleic anhydride were removed, and water was removed from the system using an azeotrope of toluene and water by heating under a reduced pressure at 70° C. or lower. Then, 2 parts of methanesulfonic acid was added, and the reaction was performed in a heated and reflux state for 2 hours. After the reaction was completed, washing with water was repeated 4 times until washing water became neutral, water was then removed from the system using an azeotrope of toluene and water by heating under a reduced pressure at 70° C. or lower, and toluene was then completely distilled off by heating under a reduced pressure, and thereby the maleimide resin (M1) represented by Formula (2) was obtained. The softening point of the obtained maleimide resin (M1) was 100° C., and the acid value was 9 mg KOH/g. Since the weight of the component having n=1 determined according to GPC analysis (RI) was 70%, and the weight of N,N'-(1,3-phenylene-di-(2,2-propylidene)-di-p-phenylene) bismaleimide in the component having n=1 determined according to HPLC analysis was 53%, the weight of N,N'-(1,3-phenylene-di-(2,2-propylidene)-di-p-phenylene) bismaleimide in the maleimide resin (M1) was 37%.

Figure 1:
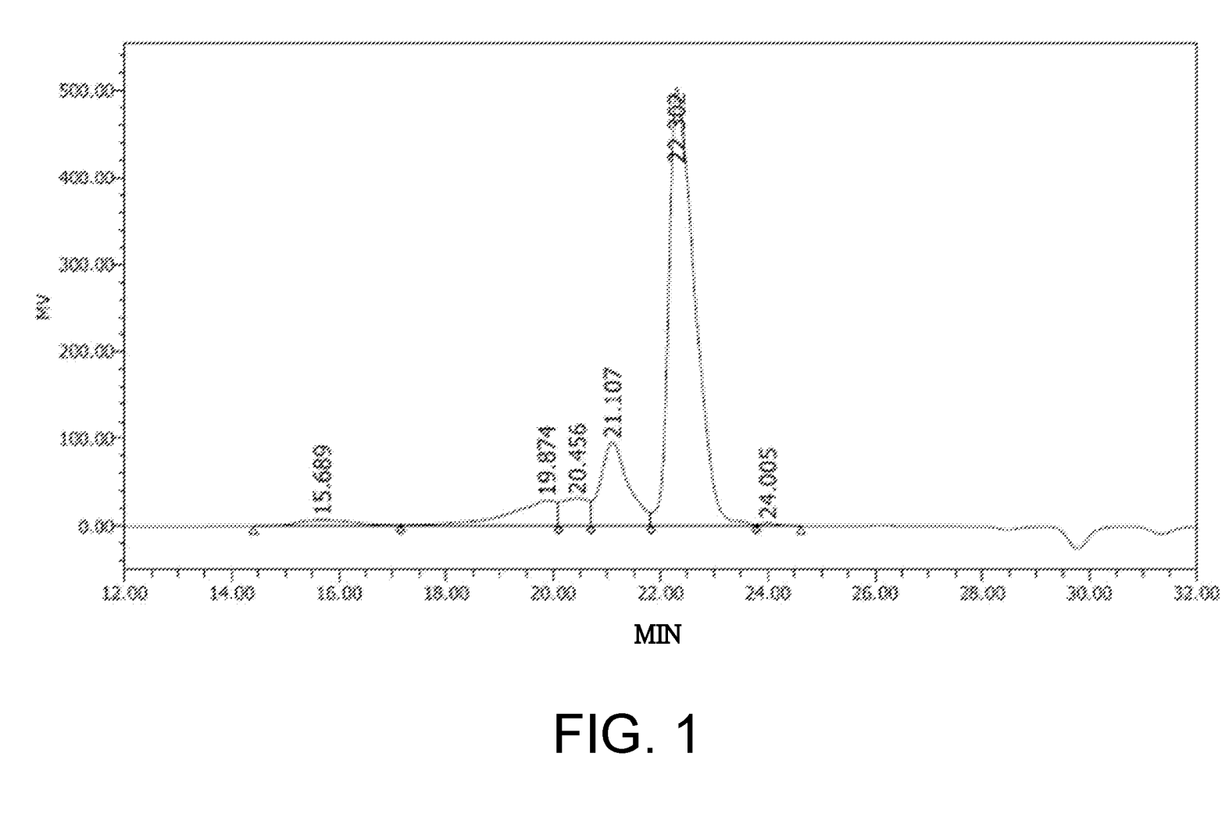
FIG. 1 shows a GPC analysis spectrum of Example 1.

FIG. 1 shows GPC analysis results. The peak with a retention time of 22.3 minutes was the peak with the component having n=1.

Figure 2:
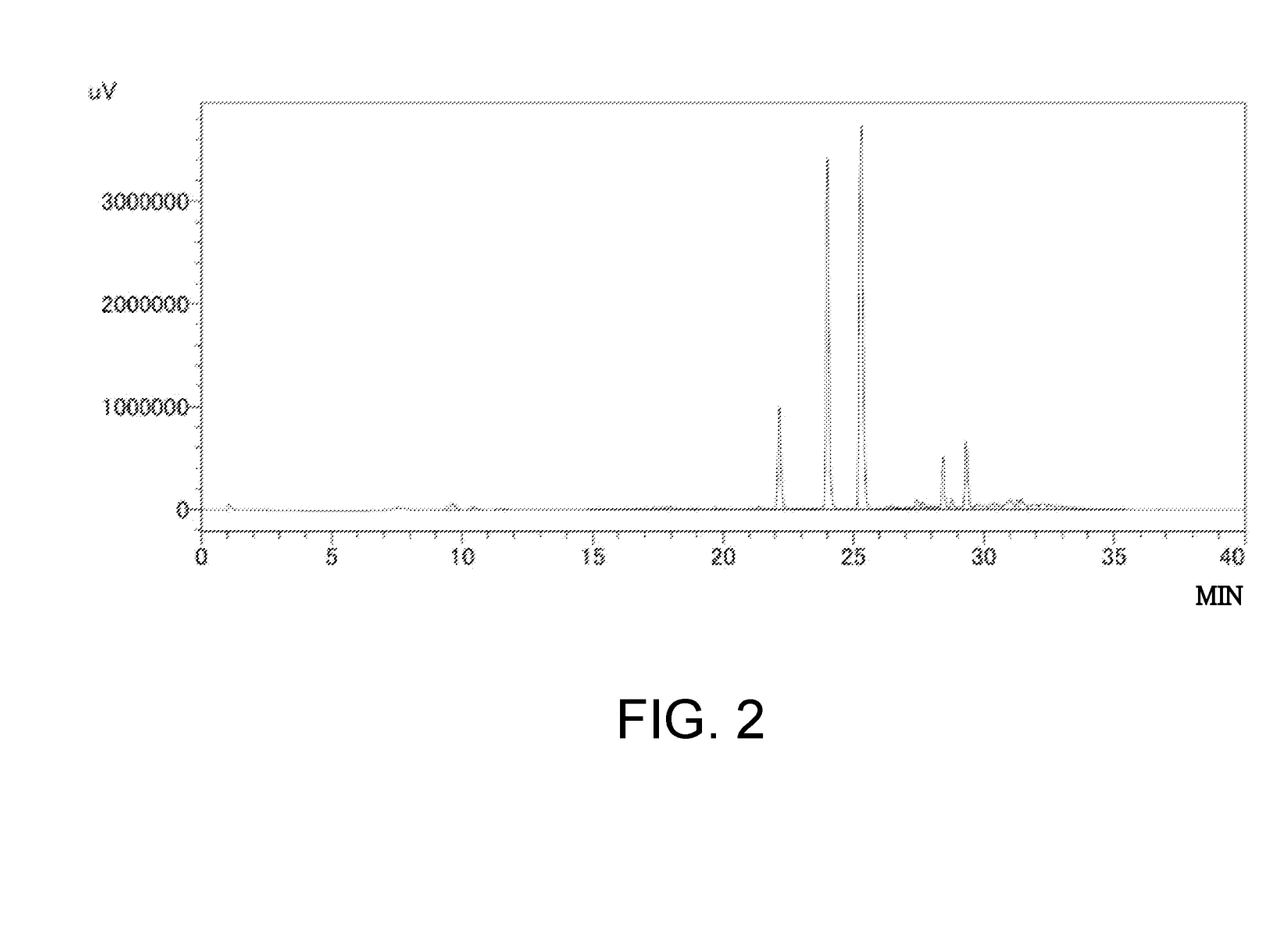
FIG. 2 shows an HPLC analysis spectrum of Example 1.

FIG. 2 shows HPLC analysis results. The peaks with retention times of 22.1 minutes, 24.0 minutes, and 25.3 minutes were peaks with the component having n=1, and the peak with a retention time of 25.3 minutes was the peak with N,N'-(1,3-phenylene-di-(2,2-propylidene)-di-p-phenylene) bismaleimide.

Example 2

The same operation as in Example 1 was performed except that 197 parts of the aromatic amine resin (A1) of Example 1 was changed to 36 parts of the aromatic amine resin (A1) and 140 parts of 1,3-bis(p-aminocumyl)benzene (A2), and a resin solution prepared by performing dissolution in 95 parts of N-methyl-2-pyrrolidone and 95 parts of toluene was changed to a resin solution prepared by performing dissolution in N-methyl-2-pyrrolidone72 parts and 100 parts of toluene, and thereby the maleimide resin (M2) represented by Formula (2) was obtained. The softening point of the obtained maleimide resin (M2) was 93° C. and the acid value was 4 mg KOH/g. Since the weight of the component having n=1 determined according to GPC analysis (RI) was 96% and the weight of N,N'-(1,3-phenylene-di-(2,2-propylidene)-di-p-phenylene)bismaleimide in the component having n=1 determined according to HPLC analysis was 92%, the weight of N,N'-(1,3-phenylene-di-(2,2-propylidene)-di-p-phenylene)bismaleimide in the maleimide resin (M2) was 88%.

Example 3

The same operation as in Example 1 was performed except that 197 parts of the aromatic amine resin (A1) of Example 1 was changed to 74 parts of the aromatic amine resin (A1) and 107 parts of 1,3-bis(p-aminocumyl)benzene (A2), and a resin solution prepared by performing dissolution in 95 parts of N-methyl-2-pyrrolidone and 95 parts of toluene was changed to a resin solution prepared by performing dissolution in 78 parts of N-methyl-2-pyrrolidone and 100 parts of toluene, and thereby the maleimide resin (M3) represented by Formula (2) was obtained. The softening point of the obtained maleimide resin (M3) was 95° C. and the acid value was 5 mg KOH/g. Since the weight of the component having n=1 determined according to GPC analysis (RI) was 80% and the weight of N,N'-(1,3-phenylene-di-(2,2-propylidene)-di-p-phenylene)bismaleimide in the component having n=1 determined according to HPLC analysis was 79%, the weight of N,N'-(1,3-phenylene-di-(2,2-propylidene)-di-p-phenylene)bismaleimide in the maleimide resin (M3) was 63%.

Example 4

The same operation as in Example 1 was performed except that 197 parts of the aromatic amine resin (A1) of Example 1 was changed to 73 parts of the aromatic amine resin (A1) and 114 parts of 1,3-bis(p-aminocumyl)benzene (A2), and a resin solution prepared by performing dissolution in 95 parts of N-methyl-2-pyrrolidone and 95 parts of toluene was changed to a resin solution prepared by performing dissolution in 84 parts of N-methyl-2-pyrrolidone and 100 parts of toluene, and thereby the maleimide resin (M4) represented by Formula (2) was obtained. The softening point of the obtained maleimide resin (M4) was 96° C. and the acid value was 7 mg KOH/g. Since the weight of the component having n=1 determined according to GPC analysis (RI) was 78% and the weight of N,N'-(1,3-phenylene-di-(2,2-propylidene)-di-p-phenylene)bismaleimide in the component having n=1 determined according to HPLC analysis was 76%, the weight of N,N'-(1,3-phenylene-di-(2,2-propylidene)-di-p-phenylene)bismaleimide in the maleimide resin (M4) was 59%.

Example 5

The same operation as in Example 1 was performed except that 197 parts of the aromatic amine resin (A1) of Example 1 was changed to 73 parts of the aromatic amine resin (A1) and 114 parts of 1,3-bis(p-aminocumyl)benzene (A2), and a resin solution prepared by performing dissolution in 95 parts of N-methyl-2-pyrrolidone and 95 parts of toluene was changed to a resin solution prepared by performing dissolution in 84 parts of N-methyl-2-pyrrolidone and 100 parts of toluene, and thereby the maleimide resin (M5) represented by Formula (2) was obtained. The softening point of the obtained maleimide resin (M5) was 98° C. and the acid value was 8 mg KOH/g. Since the weight of the component having n=1 determined according to GPC analysis (RI) was 74% and the weight of N,N'-(1,3-phenylene-di-(2,2-propylidene)-di-p-phenylene)bismaleimide in the component having n=1 determined according to HPLC analysis was 70%, the weight of N,N'-(1,3-phenylene-di-(2,2-propylidene)-di-p-phenylene)bismaleimide in the maleimide resin (M5) was 52%.

Synthesis Example 3

147 parts of maleic anhydride, 300 parts of toluene, and 3.3 parts of methanesulfonic acid were put into a flask having a thermometer, a cooling pipe, a Dean-Stark azeotropic distillation trap, and a stirrer attached thereto and brought into a heated and reflux state. Then, a resin solution prepared by dissolving 172 parts of 1,3-bis(p-aminocumyl) benzene (A2) in 66 parts of N-methyl-2-pyrrolidone and 100 parts of toluene was added dropwise over 3 hours while maintaining a reflux state. During this period, condensed water and toluene which formed an azeotrope under reflux conditions were cooled and liquid-separated in the Dean-Stark azeotropic distillation trap, and then toluene on the organic layer was returned into the system, and water was discharged to the outside of the system. After dropwise addition of the resin solution was completed, the reaction was performed for 2 hours while maintaining a reflux state and performing a dehydration operation.

After the reaction was completed, washing with water was repeated 4 times, methanesulfonic acid and excess maleic anhydride were removed, and water was removed from the system using an azeotrope of toluene and water by heating under a reduced pressure at 70° C. or lower. Then, 1.7 parts of methanesulfonic acid was added and the reaction was performed in a heated and reflux state for 2 hours. After the reaction was completed, washing with water was repeated 3 times until washing water became neutral, water was then removed from the system using an azeotrope of toluene and water by heating under a reduced pressure at 70° C. or lower, toluene was then completely distilled off by heating under a reduced pressure, and thereby 237 parts of the maleimide resin (M6) was obtained. The softening point of the obtained maleimide resin (M6) was 91° C., and the acid value was 3 mg KOH/g. Since the weight of the component having n=1 determined according to GPC analysis (RI) was 98% and the weight of N,N'-(1,3-phenylene-di-(2,2-propylidene)-di-p-phenylene)bismaleimide in the component having n=1 determined according to HPLC analysis was 100%, the weight of N,N'-(1,3-phenylene-di-(2,2-propylidene)-di-p-phenylene)bismaleimide in the maleimide resin (M6) was 98%.

Figure 3:
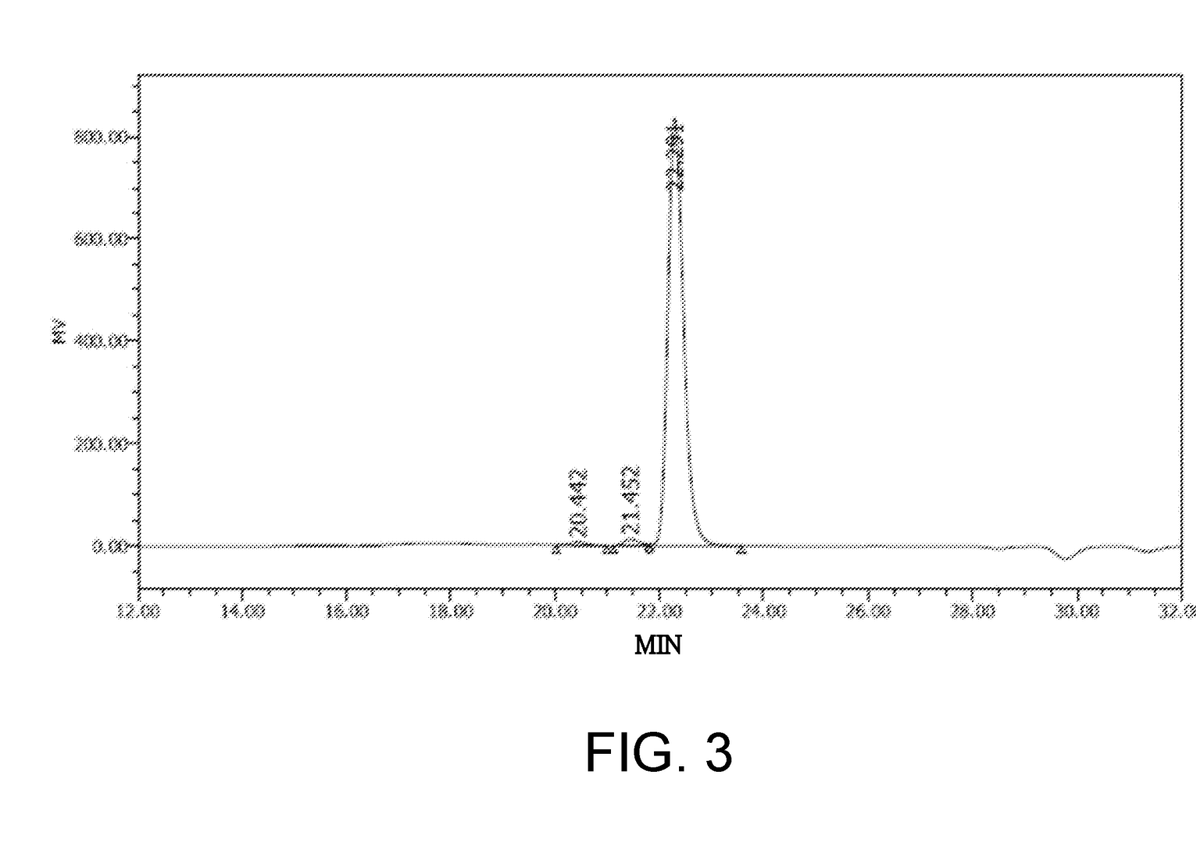
FIG. 3 shows a GPC analysis spectrum of Synthesis Example 3.

FIG. 3 shows GPC analysis results. The peak with a retention time of 22.3 minutes was the peak with the component having n=1.

Figure 4:
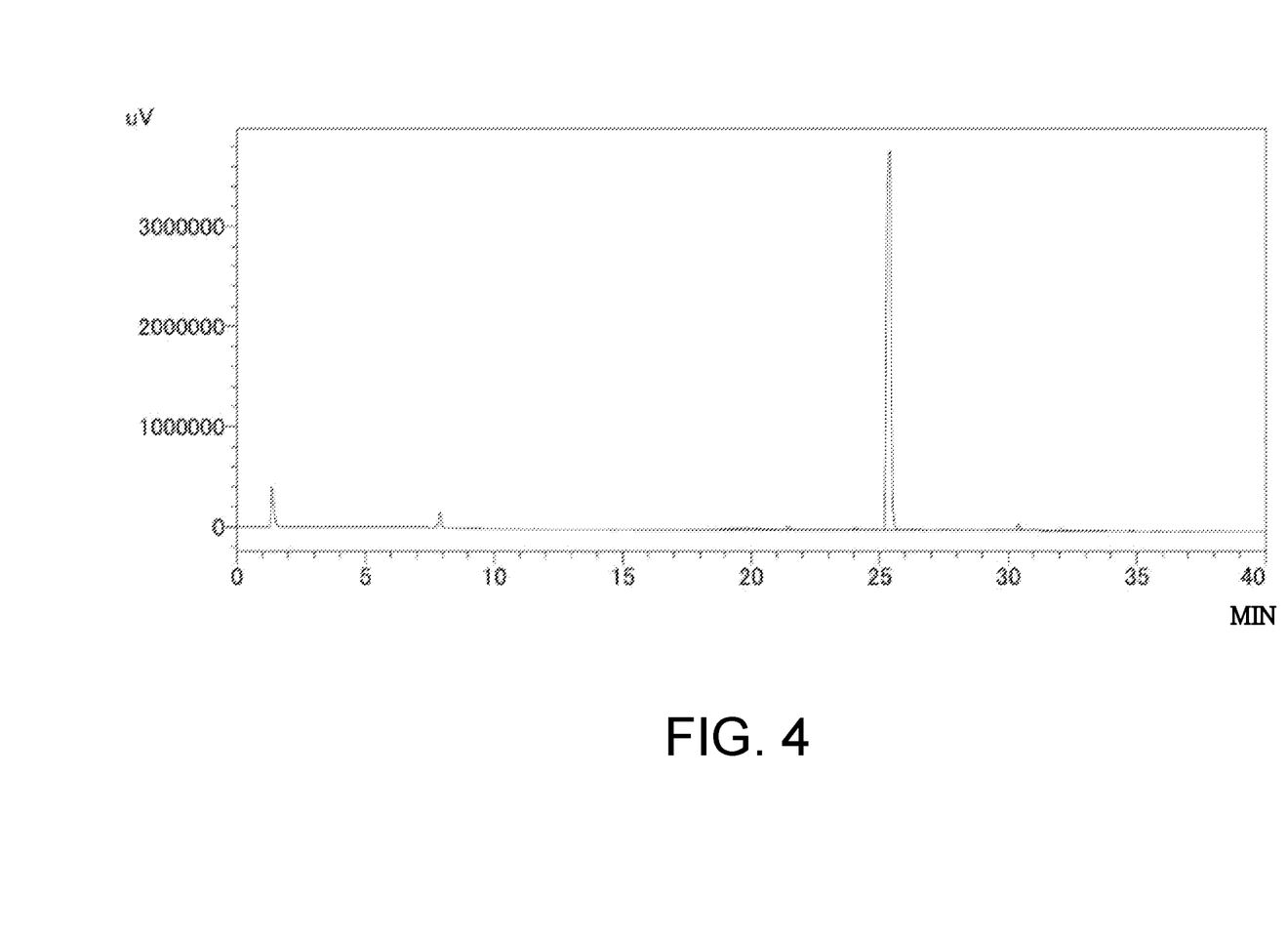
FIG. 4 shows an HPLC analysis spectrum of Synthesis Example 3.

FIG. 4 shows HPLC analysis results. The peak with a retention time of 25.4 minutes was the peak with the component having n=1, and the peak with a retention time of 25.4 minutes was the peak with N,N'-(1,3-phenylene-di-(2,2-propylidene)-di-p-phenylene) bismaleimide.

Examples 6 to 10 and Comparative Example 1

The maleimide resins obtained in the examples and the synthesis examples were dissolved in toluene or methyl ethyl ketone (MEK) so that the resin content was 60%, and the number of days until precipitates occurred at room temperature was observed for 14 days, and the results are shown in Table 1.

Based on the results of Table 1, it was confirmed that Examples 6 to 10 had favorable solution stability in toluene or MEK. In particular, it was confirmed that Examples 6, 8 to 10 had favorable solution stability in both toluene and MEK.

Example 11 and Comparative Example 2

The maleimide resin (M1) obtained in Example 1 and maleimide resin (M6) obtained in Synthesis Example 3 were used, various epoxy resins, curing agents, and curing accelerators were incorporated in proportions (parts by weight) in Table 1, kneaded with mixing rollers, and formed into tablets, and then transferred and molded to prepare resin molded products and the products were cured at 200° C. for 2 hours. Physical properties of the cured product obtained in this manner were measured according to the following items and the results are shown in Table 2.

Glass transition temperature (Tg): measured using TMA-Q400EM (thermo-mechanical measurement device commercially available from TA-instruments) at a heating rate of 2° C./min Td5 (5% thermogravimetric reduction temperature): the obtained cured product was pulverized into a powder, and the thermal decomposition temperature thereof was measured using a sample having a 100-mesh path and 200-mesh on through TG-DTA. The temperature at which the weight was reduced by 5% when a sample amount of 10 mg was measured at a heating rate of 10° C./min, and an air volume of 200 ml/hr.

Water absorption rate: weight increase rate (%) before and after boiling a disk-shaped test piece having a diameter of 5 cm and a thickness of 4 mm in water at 100° C. for 24 hours.

Dielectric constant and dielectric loss tangent: measured according to (cavity resonator commercially available from Agilent Technologies) JIS C2565 at 1 GHz

TABLE 2

|  |  | Example 11 | Comparative Example 2 |
|---|---|---|---|
| Formulation amount | | | |
| M1 | | 70 | |
| M6 | | | 70 |
| E1 | | 30 | 30 |
| P1 | | 22 | 22 |
| 2E4MZ | | 1.8 | 1.8 |
| Evaluation test results | | | |
| Glass transition temperature | ° C. | 157 | 143 |
| Td5 | ° C. | 357 | 350 |
| Water absorption rate (100° C.) | % | 1.30 | 1.40 |
| Dielectric constant (1 GHz) | % | 2.93 | 2.96 |
| Dielectric loss tangent (1 GHz) | | 0.0094 | 0.0098 |

E1: NC-3000-L (commercially available from Nippon Kayaku Co., Ltd., an epoxy equivalent of 270 g/eq)

TABLE 1

|  | Example 6 | Example 7 | Example 8 | Example 9 | Example 10 | Comparative Example 1 |
|---|---|---|---|---|---|---|
| Maleimide resin | M1 | M2 | M3 | M4 | M5 | M6 |
| Toluene | No precipitate | 1 day | No precipitate | No precipitate | No precipitate | 1 day |
| MEK | No precipitate | No precipitate | No precipitate | No precipitate | No precipitate | 1 day |

P1: Kayahard GPH-65 (commercially available from Nippon Kayaku Co., Ltd., hydroxy group equivalent of 200 g/eq)

2E4MZ: 2-ethyl-4-methylimidazole (commercially available from Tokyo Chemical Industry Co., Ltd.)

Based on the results of Table 2, it was confirmed that Example 11 had better results in the heat resistance, low hygroscopicity, and dielectric characteristics than Comparative Example 2.

Example 12 and Comparative Examples 3 and 4

Figure 5:
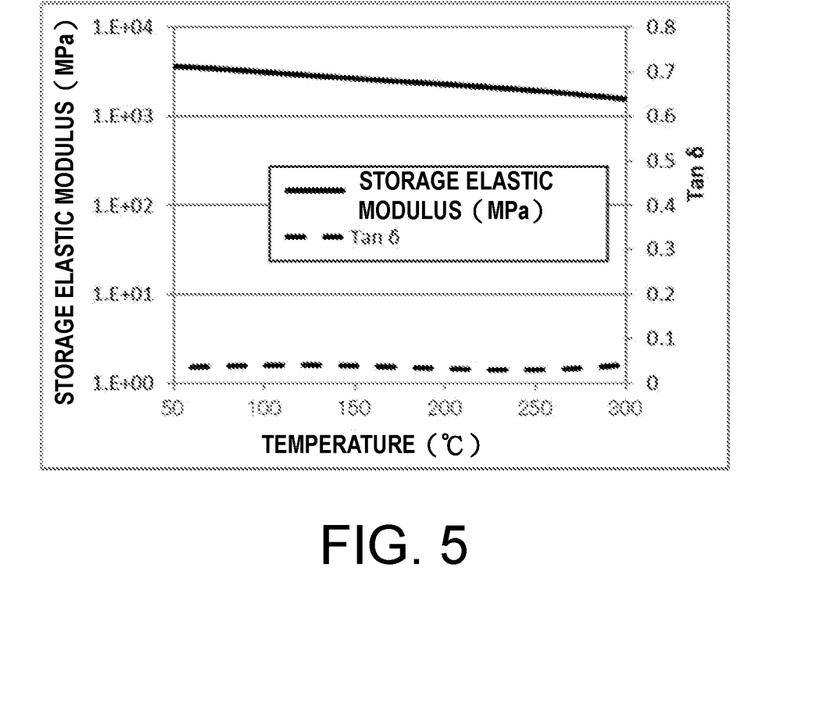
FIG. 5 shows a DMA chart of Example 12.
Figure 6:
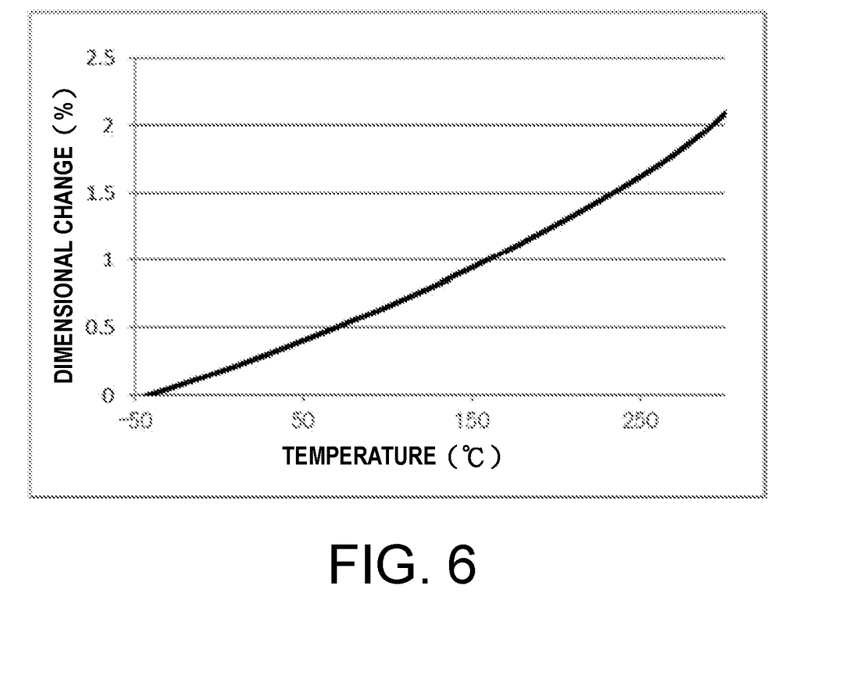
FIG. 6 shows a TMA chart of Example 12.

According to proportions (parts by weight) shown in the following Table 3, maleimide resins (M1, M6, BMI-2300 (polyphenylmethane maleimide, commercially available from Daiwa Fine Chemicals Co., Ltd.)), MEK (methyl ethyl ketone), and a catalyst (DCP; dicumyl peroxide, commercially available from Kayaku Nouryon Corporation) were mixed and formed into films having a thickness of 30 μm using an applicator, and the solvent was then removed at 120° C., and the films were collected. Subsequently, the films were pulverized and formed into tablets, and resin molded products were prepared by transfer molding, and then cured at 250° C. for 2 hours. Physical properties of the cured product obtained in this manner were measured according to the following items and the results are shown in Table 3. In addition, FIG. 5 shows DMA measurement results of the cured product of Example 12 and FIG. 6 shows TMA measurement results.

- Dielectric constant and dielectric loss tangent: measured according to (cavity resonator commercially available from Agilent Technologies) JIS C2565 at 1 GHz and 10 GHz
- DMA measurement: measured by DMA-2980 (dynamic viscoelasticity measurement instrument: commercially available from TA-instruments) at a heating rate of 2° C./min
- TMA measurement: measured by TMA-Q400EM (thermo-mechanical measurement device: commercially available from TA-instruments) at a heating rate of 2° C./min

TABLE 3

|  | | Example 12 | Comparative Example 3 | Comparative Example 4 |
|---|---|---|---|---|
| Formulation amount | | | | |
| M1 | | 60 | | |
| M6 | | | 60 | |
| BMI-2300 | | | | 30 |
| MEK | | 40 | 40 | 70 |
| DCP | | 2 | 2 | 2 |
| Evaluation test results | | | | |
| Dielectric constant (1 GHz) | % | 2.71 | 2.72 | 3.01 |
| Dielectric loss tangent (1 GHz) | | 0.0017 | 0.0020 | 0.0054 |
| Dielectric constant (10 GHZ) | % | 2.66 | 2.68 | 2.91 |
| Dielectric loss tangent (10 GHz) | | 0.0019 | 0.0026 | 0.0057 |

Based on the results of Table 3, it was confirmed that Example 12 had an excellent dielectric characteristics. In addition, based on the results of FIGS. 5 and 6, it was confirmed that Example 12 had excellent heat resistance because no glass transition temperature was observed at 300° C. or higher and physical properties at a high temperature could be maintained.

Examples 13 to 17 and Comparative Examples 5 to 14

According to proportions (parts by weight) shown in the following Table 4, maleimide resins (M1, M6, BMI-2300 (polyphenylmethane maleimide, commercially available from Daiwa Fine Chemicals Co., Ltd.)), various resins, a catalyst, and a solvent were incorporated, the mixture was stirred at room temperature and completely melted to produce varnishes.

Table 4 shows the results of the following evaluations of the obtained varnishes.

- Solubility: It was checked whether the obtained varnish was compatible.
  - ○: The varnish was transparent Δ: Slightly cloudy x: There was sediment
- Storage performance: It was checked whether there were precipitates when the obtained varnish was stored at room temperature for 1 week.
  - ○: No precipitates x: There were precipitates
- Curability: it was checked whether the cured product was soluble when the obtained varnish was cured under curing conditions of 200° C. for 2 hours and then impregnated with MEK (methyl ethyl ketone) for 24 hours.
  - ○: Cured product did not dissolve x: Cured product dissolved

TABLE 4

| | Example 13 | Example 14 | Example 15 | Example 16 | Example 17 | Comparative Example 5 | Comparative Example 6 | Comparative Example 7 | Comparative Example 8 | Comparative Example 9 | Comparative Example 10 | Comparative Example 11 | Comparative Example 12 | Comparative Example 13 | Comparative Example 14 |
|---|---|---|---|---|---|---|---|---|---|---|---|---|---|---|---|
| | Formulation amount | | | | | | | | | | | | | | |
| M1 | 60 | 40 | 40 | 40 | 60 | | | | | | | | | | |
| M6 | | | | | | 60 | | | | | | | | | |
| BMI-2300 | | | | | | | 40 | 40 | 40 | 60 | 60 | 40 | 40 | 40 | 60 |
| JER-828 | | 20 | | 20 | | | 20 | | 20 | | | 20 | | 20 | |
| SA-90 | | 20 | 30 | 20 | | | 20 | 30 | 20 | | | 20 | 30 | 20 | |
| SA-9000-111 | 40 | | 30 | | | 40 | | 30 | | | 40 | | 30 | | |
| R-684 | | | | | 40 | | | | | 40 | | | | | 40 |
| BPACA | | 20 | | 20 | | | 20 | | 20 | | | 20 | | 20 | |
| Unifiner M | | | | | | | | | | | | | | | |
| DCP | 1 | 1 | 1 | 1 | 1 | 1 | 1 | 1 | 1 | 1 | 1 | 1 | 1 | 1 | 1 |
| 2E4MZ | | 0.5 | | | | | 0.5 | | | | | 0.5 | | | |
| Manganese naphthenate | | | | | | | | | | | | | | | |
| Toluene | 100 | 70 | 100 | 100 | 100 | 100 | 70 | 100 | 100 | 100 | 100 | 70 | 100 | 100 | 100 |
| MEK | | 30 | | | | | 30 | | | | | 30 | | | |
| | Evaluation test results | | | | | | | | | | | | | | |
| Solubility | ○ | ○ | ○ | ○ | ○ | △ | △ | △ | △ | × | × | × | △ | △ | × |
| Storage performance | ○ | ○ | ○ | ○ | ○ | × | × | × | × | × | × | × | × | × | × |
| Curability | ○ | ○ | ○ | ○ | ○ | ○ | ○ | ○ | ○ | ○ | ○ | ○ | ○ | ○ | ○ |

JER-828: Bisphenol A type epoxy resin (commercially available from Mitsubishi Chemical Corporation)
SA-90: phenolic modified polyphenylene ether resin (commercially available from SABIC)
SA-9000-111: modified polyphenylene ether resin (commercially available from SABIC)
R-684: dicyclopentanyl diaciylate (commercially available from Nippon Kayaku Co., Ltd.)
BPACA: 2,2-bis(4-cyanatophenyl)propane (reagent commercially available from Tokyo Chemical Industry Co., Ltd.)
DCP: dicumyl peroxide (commercially available from Kayaku Nouryon Corporation)
Manganese naphthenate: (reagent commercially available from Tokyo Chemical Industry Co., Ltd.)

Example 18

In addition, the varnish obtained in Example 13 was applied onto a PET film with a thickness of 100 μm, and cured in an oven under conditions of 120° C. 30 minutes+160° C. 30 minutes+220° C. for 2 hours while removing the solvent, and thereby a resin film was obtained. Physical properties of the cured product obtained in this manner were measured according to the following items and the results are shown in Table 5.

Glass transition temperature (Tg): the temperature when tan δ was the maximum value was measured by a dynamic viscoelasticity test machine (DMA-2980, commercially available from TA-instruments) at a heating rate of 2° C./min Dielectric constant and dielectric loss tangent: measured according to (cavity resonator, commercially available from Agilent Technologies) JIS C2565 at 10 GHz

TABLE 5

|  |  | Example 18 |
| --- | --- | --- |
| Glass transition temperature | ° C. | 278 |
| Dielectric constant (10 GHz) | % | 2.5 |
| Dielectric loss tangent (10 GHZ) |  | 0.0012 |

Based on the results of Table 4, it was confirmed that Examples 13 to 17 were excellent in all of solubility, storage performance, and curability. In addition, based on the results of Table 5, it was confirmed that Example 18 had excellent heat resistance and electrical characteristics.

INDUSTRIAL APPLICABILITY

The maleimide resin of the present invention has high workability due to excellent solution stability and has excellent heat resistance, low hygroscopicity, and dielectric characteristics, and thus it is suitably used for an electrical and electronic component such as a semiconductor encapsulant, a printed wiring board, and a build-up laminated plate and a lightweight and high strength material such as a carbon fiber-reinforced plastic and a glass fiber-reinforced plastic.

What is claimed is:

1. A maleimide resin represented by following Formula (1) and in which a content (A1) of the component having n=1 in formula (1) as determined by GPC analysis, a content (A2) of N,N'-(phenylene-di-(2,2-propylidene)-di-p-phenylene)bismaleimide in the component having n=1 as determined by HPLC analysis, a content of N,N'-(phenylene-di-(2,2-propylidene)-di-p-phenylene)bismaleimide from the calculation formula of (A1)×(A2) is 90 area % or less:

in Formula (1), n represents the number of repetitions, and 1≤n<5.

2. The maleimide resin according to claim 1, wherein a content of a component having n=1 in Formula (1) is 98 area % or less.

3. A maleimide resin represented by following Formula (2) and in which a content of N,N'-(1,3-phenylene-di-(2,2-propylidene)-di-p-phenylene)bismaleimide is 90 area % or less:

in Formula (2), n represents a number of repetitions, and 1≤n<5.

4. The maleimide resin according to claim 3, wherein a content of a component having n=1 in Formula (2) is 98 area % or less.

5. A curable resin composition containing the maleimide resin according to claim 1.

6. The curable resin composition according to claim 5, further comprising
a curing agent.

7. A cured product obtained by curing the curable resin composition according to claim 5.

8. A curable resin composition containing the maleimide resin according to claim 2.

9. A curable resin composition containing the maleimide resin according to claim 3.

10. A curable resin composition containing the maleimide resin according to claim 4.

11. The curable resin composition according to claim 9, further comprising
a curing agent.

12. A cured product obtained by curing the curable resin composition according to claim 6.

13. A cured product obtained by curing the curable resin composition according to claim 9.

14. A cured product obtained by curing the curable resin composition according to claim 11.

* * * * *